(12) United States Patent
McKay (10) Patent No.: US 8,617,252 B2
(45) Date of Patent: *Dec. 31, 2013

(54) SPINAL FUSION METHODS AND DEVICES

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 619 days.

This patent is subject to a terminal disclaimer.

(21) Appl. No.: 12/537,701

(22) Filed: Aug. 7, 2009

(65) Prior Publication Data

US 2009/0298777 A1    Dec. 3, 2009

Related U.S. Application Data (63) Continuation of application No. 10/399,830, filed as application No. PCT/US01/46044 on Oct. 24, 2001, now Pat. No. 8,226,729.

(60) Provisional application No. 60/242,794, filed on Oct. 24, 2000.

(51) Int. Cl.
*A61F 2/28* (2006.01)
*A61F 2/02* (2006.01)

(52) U.S. Cl.
USPC ............... 623/23.61; 623/17.11; 623/23.75

(58) Field of Classification Search
None
See application file for complete search history.

(56) References Cited

U.S. PATENT DOCUMENTS 3,787,900 A * 1/1974 McGee .................. 424/422
4,394,370 A   7/1983 Jefferies (Continued)

FOREIGN PATENT DOCUMENTS

DE    4216496 A1    11/1993
WO    9315767 A1    8/1993

(Continued)

OTHER PUBLICATIONS

Schimandle, Jeffrey H. et al., "Experimental Spinal Fusion With Recombinant Human Bone Morphogenetic Protein-2", Spine, vol. 20, No. 12, pp. 1326-1337, 1995, discloses BMP-2 buffered in LF-6 buffer from Genetics Institute soaked onto a collagen sponge, J.B. Lippincott Company.

(Continued)

*Primary Examiner* — David H Willse
*Assistant Examiner* — Javier Blanco
(74) *Attorney, Agent, or Firm* — Sorell Lenna & Schmidt LLP (57) ABSTRACT

Methods, devices and compositions for fusing adjacent vertebrae, and otherwise localizing bone growth, are provided. In one form of the invention, a method for fusing adjacent vertebrae includes preparing a disc space for receipt of an intervertebral disc implant in an intervertebral disc space between adjacent vertebrae, inserting the implant into the intervertebral disc space and providing an osteoinductive composition that includes an osteoinductive factor in a pharmaceutically acceptable carrier. The carrier is advantageously substantially impermeable to efflux of the osteoinductive factor and is released as the carrier is resorbed or biodegraded. Preferred carriers include a hardened, resorbable carrier, such as a calcium phosphate cement that retains at least about 50% of the osteoinductive factors greater than about 2 days. Preferred osteoinductive factors are growth factors and include bone morphogenetic proteins and LIM mineralization proteins. In alternative forms of the invention, the method may be performed without utilization of a load-bearing spinal implant by disposing the osteoinductive composition in the disc space. The method is advantageously performed on lumbar vertebrae by a posterior approach. Intervertebral fusion devices and methods for their preparation are also provided.

6 Claims, 6 Drawing Sheets

(56) References Cited

U.S. PATENT DOCUMENTS

| | | | |
|---|---|---|---|
| 4,673,355 A * | 6/1987 | Farris et al. | 433/218 |
| 5,290,763 A | 3/1994 | Poser et al. | |
| 5,290,764 A | 3/1994 | Duke, Jr. et al. | |
| 5,609,636 A | 3/1997 | Kohrs et al. | |
| 5,683,461 A | 11/1997 | Lee et al. | |
| 5,776,193 A | 7/1998 | Kwan et al. | |
| 5,876,452 A | 3/1999 | Athanasiou et al. | |
| 6,027,742 A | 2/2000 | Lee et al. | |
| 6,294,187 B1 | 9/2001 | Boyce et al. | |
| 6,344,061 B1 | 2/2002 | Leitao et al. | |
| 6,344,209 B1 | 2/2002 | Saito et al. | |
| 6,679,918 B1 | 1/2004 | Benedict et al. | |
| 2004/0081704 A1 | 4/2004 | Benedict et al. | |
| 2008/0293617 A1 | 11/2008 | Benedict et al. | |

FOREIGN PATENT DOCUMENTS

| | | |
|---|---|---|
| WO | 9713533 A1 | 4/1997 |
| WO | 9817209 A2 | 4/1998 |
| WO | 9817330 A1 | 4/1998 |
| WO | 9853768 A1 | 12/1998 |

OTHER PUBLICATIONS

Nevins, et al, "Bone Formation in the Goat Maxillary Sinus Induced by Absorbable Collagen Sponge Implants Impregnated with Recombinant Human Bone Morphogenetic Protein-2," The International Journal of Periodontics & Restorative Dentistry, vol. 16, No. 1, pp. 8-19 (1996)—discloses soaking a collagen sponge with rhBMP-2 in a buffer from Genetics Institute.

Sigurdsson, et al., "Periodontal Repair in Dogs: Evaluation of rhBMP-2 Carriers," The International Journal of Periodontics & Restorative Dentistry, vol. 16, No. 6, pp. 524-537 (1996)—discloses rhBMP-2 in buffer soaked onto an absorbable collagen sponge of type I bovine collagen (Helistat).

Boyne, et al., "A Feasibility Study Evaluating rhBMP-2/Absorbable Collagen Sponge for Maxillary Sinus Floor Augmentation," The International Journal of Periodontics & Restorative Dentistry, vol. 17, No. 1, pp. 11-25 (1997)—discloses soaking 3.4 mg of rhBMP-2 (from a 0.43 mg/ml buffered solution available from Genetics Institute) onto a 7.5×10 cm bovine type I collagen sponge (either 0.01 or 0.06 mmol acid/100 mg collagen)19.

Sellers, et al., "The Effect of Recombinant Human Bone Morphogenetic Protein-2 (rhBMP-2) on the Healing of Full-Thickness Defects of Articular Cartilage," The Journal of Bone & Joint Surgery, 79-A, pp. 1452-1463 (1997)—discloses filling a 3mm wide by 3mm deep defect with bovine type-I collagen sponge soaked with 5 u.g rhBMP-2 in buffer (30 mM L-glutamic acid, 2.5% glycine, 0.5% sucrose, and 0.01% Tween 80, pH 4.5).

* cited by examiner

SPINAL FUSION METHODS AND DEVICES

CROSS-REFERENCE TO RELATED APPLICATIONS

The present application is a continuation of U.S. patent application Ser. No. 10/399,830 filed on Jul. 25, 2003 now U.S. Pat. No. 8,226,729, which is the U.S. national phase filing of PCT International Application Number US01/46044 filed on Oct. 24, 2001, which claims the benefit of U.S. Provisional Application No. 60/242,794 filed Oct. 24, 2000, which are hereby incorporated by reference in their entirety into the present disclosure.

BACKGROUND OF THE INVENTION

The present invention relates generally to methods and devices for stabilizing the spine. More specifically, the invention provides methods and devices for fusing adjacent vertebrae and for localizing spinal bone growth.

Back pain affects millions of individuals and is a common cause of disability for the middle-aged working population. A frequent cause of back pain is rupture or degeneration of intervertebral discs.

Intervertebral discs, located between the endplates of adjacent vertebrae, stabilize the spine, distribute forces between vertebrae and cushion vertebral bodies. An intervertebral disc includes the nucleus pulposus, a gelatinous component that is surrounded and confined by an outer, fibrous ring, called the annulus fibrosus. In a healthy, undamaged spine, the annulus fibrosus prevents the nucleus pulposus from protruding outside the disc space.

Spinal discs may be displaced or damaged due to trauma, disease, or aging. Disruption of the annulus fibrosus allows the nucleus pulposus to protrude into the vertebral canal; a condition commonly referred to as a herniated or ruptured disc. The extruded nucleus pulposus may press on a spinal nerve, which may result in nerve damage, pain, numbness, muscle weakness and paralysis. Intervertebral discs may also deteriorate due to the normal aging process or disease. As a disc dehydrates and hardens, the disc space height will be reduced leading to instability of the spine, decreased mobility and pain.

In many instances, the only relief from the symptoms of these conditions is a discectomy, or surgical removal of all or a portion of an intervertebral disc followed by fusion of the adjacent vertebrae. The removal of the damaged or unhealthy disc will allow the disc space to collapse. Collapse of the disc space can cause instability of the spine, abnormal joint mechanics, premature development of arthritis or nerve damage, in addition to severe pain. Pain relief afforded by a discectomy and arthrodesis requires preservation of the disc space and eventual fusion of the affected motion segments.

One solution to the stabilization of an excised disc space is to fuse the vertebrae between their respective endplates. Typically an osteoinductive material is implanted at the treatment site to promote spinal fusion. Success of the discectomy and fusion procedure requires development of a contiguous growth of bone to create a solid mass capable of withstanding the compressive loads on the spine for the life of the patient.

Additionally, several metal spacers have been developed for implantation into a disc space and can be used to promote fusion. Medtronic Sofamor Danek, Inc., (Memphis, Tenn.) markets a number of hollow spinal cages, and a wide variety of other such cages are known in the art. For example, U.S. Pat. Nos. 5,015,247 and 5,984,967 to Michelson et al. and Zdeblick et al., respectively, disclose threaded spinal cages. The cages are hollow and can be filled with osteoinductive material, such as autograft, allograft and/or material isolated from the grafts. Apertures defined in the cages communicate with the hollow interior to provide a path for tissue growth between the vertebral endplates.

Such implants have been positioned in vivo by medical procedures well known in the art, including anterior and posterior approaches. In certain instances, it is possible that the osteoinductive material that includes an osteoinductive factor may diffuse, or otherwise migrate, from the implant into undesired locations, which may result in bone formation in these locations. For example, the osteoinductive material may diffuse out of the cage, or other implant, and may form bone inside an adjacent hematoma, or tissue, such as fibrous scar tissue. The can be an increased risk of hematoma formation with posterior lumbar interbody fusion (PLIF) or transforaminal lumbar interbody fusion procedure, because the blood released during these procedures can pool in the spinal canal or foramen space. Scar tissue formation from pooling blood from prior surgeries is also more prone in revision PLIF or TLIF procedures. There is therefore a need for methods for fusing adjacent vertebrae and osteoinductive compositions that aid in reducing formation of bone tissue in unwanted, or otherwise undesired, locations.

In light of the above described problems, there is a continuing need for advancements in the relevant field, including improved methods for treating orthopedic injuries and defects, osteogenic compositions and devices relating to enhancing spinal fusion. The present invention is such an advancement and provides a wide variety of benefits and advantages.

SUMMARY OF THE INVENTION

It has been discovered that blending osteoinductive compositions with a slow release carrier can effectively reduce bone formation in undesired locations during spinal fusion procedures. For example the slow release carrier can inhibit migration of the entrained osteoinductive composition to tissue adjacent the treatment site, for example, sites of hematoma, scar tissues, or other fibrous tissues that are a distance from, or adjacent to, the desired site for fusion. Accordingly, one aspect of the invention provides methods for fusing adjacent vertebrae, and otherwise localizing bone growth, in an interbody fusion procedure. The method is particularly advantageous for treatment sites that already exhibit a localized hematoma or scar tissues or exhibit a clinical predisposition for such. During the disc space preparation, a hematoma site or scar tissue site can be exposed or evaluated for a predisposition for bone tissue growth induced by a diffusible osteoinductive factor. In one embodiment, an osteoinductive composition and a carrier composite can be formulated to promote and limit bone growth to a desired treatment site. In another embodiment, an implant can be advantageously formulated and configured to retain an osteoinductive composition. The osteoinductive composition is therefore provided to and carried by the implant minimizing undesirable migration of the osteoinductive composition from the implant.

In other forms the invention provides minimally invasive methods for fusing adjacent vertebrae. The method comprises preparing a disc space for receipt of an osteoinductive composition and the osteoinductive composition is inserted into the prepared disc space, without utilization of a load-bearing spinal implant. Such methods may be used in conjunction with instrumentation of the spine, such as anterior or posterior instrumentation with rods, plates and the like.

A composition for use in the invention includes a carrier and an effective amount of an osteoinductive material or an osteoinductive factor. The osteoinductive material can be entrapped or entrained within the carrier. The carrier is preferably substantially impermeable to efflux of the osteoinductive factor. In one embodiment, the osteogenic material is released from the carrier as the carrier is degraded or resorbed. In one embodiment, bone formation can be substantially confined to the original volume or space occupied by the carrier, osteogenic material. Migration of the osteogenic material to the hematoma site or scar tissue site is significantly reduced or eliminated. In another embodiment of the invention, the carrier is a resorbable cement and the osteogenic material is an osteoinductive factor or bone morphogenetic protein.

In other forms the invention provides methods for performing a posterior lumbar interbody fusion or a transforaminal lumbar interbody fusion, wherein the selected disc for treatment is a lumbar disc.

Intervertebral fusion devices that include a spinal implant and the osteoinductive compositions described above are also provided, as are methods of preparing the fusion device.

DESCRIPTION OF THE EMBODIMENTS

For the purposes of promoting an understanding of the principles of the invention, reference will now be made to embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

The present invention relates to methods and devices for treating adjacent vertebrae. In preferred forms of the invention, methods are provided for fusing adjacent vertebrae by a posterior or transforaminal interbody fusion approach, such as a posterior lumbar interbody fusion (PLIF) or transforaminal lumbar interbody fusion (TLIF) approach. Methods for localizing bone formation to a pre-selected location in an intervertebral disc fusion procedure are also provided. In certain forms of the invention, the methods described herein may also be performed posterolaterally or anterolaterally. In preparing the disc space in a posterior or transforaminal interbody fusion procedure, tissue can be exposed that is susceptible to or is predisposed to undesirable bone tissue growth. Desirable bone tissue growth is promoted by blending, dispersing or otherwise entraining a selected osteoinductive material with a carrier that does not allow substantial efflux of the material or an active portion of the material from the carrier. In one form, the osteoinductive material slowly diffuses out of the carrier. In another form the carrier does not release a substantial portion of the osteoinductive material, but rather as the carrier degrades and/or is bioabsorbed and gradually exposes the entrained osteoinductive material to the treatment site.

Tissue that has a predisposition to bone growth includes scar tissue that can preexist from a previous surgery or other incident disease(s) or injury causing formation thereof. The scar tissue can form, or be otherwise located, at a site a distance from, typically adjacent to, a desired site of bone formation. For example, scar tissue may have formed because of fibroblast invasion into a blood clot or hematoma from a prior surgery.

Furthermore, a hematoma can be formed during or a result of the current surgery described herein or a prior surgical procedure, disease and/or trauma. The hematoma can be created, or otherwise located a distance from, or adjacent to, the desired bone formation site. For example, tissue injured or bruised during the surgical procedure seeps blood and other fluid, and this tissue can continue to seep blood/fluid subsequent to surgical closure. This blood/fluid can pool and collect in tissue cavities and pockets such as in the spinal canal and foramen space.

It is often desirable to minimize diffusion of osteoinductive compositions into a hematoma or scar tissue because these compositions can induce calcification of the hematoma or scar tissue into bone tissue.

In one aspect of the invention, methods for fusing adjacent vertebrae, and otherwise localizing bone growth, are provided. In one form of the invention, the vertebrae are fused by a PLIF or TLIF procedure. A patient is first prepared for the surgical procedure. For example, the patient is properly positioned on the operating table, typically in a prone position with their pelvis parallel to the floor. Access to the vertebral level to be fused, such as the selected lumbar disc, is then gained utilizing surgical methodology and tools. The intervertebral disc space and adjacent vertebrae are then prepared for receipt of an intervertebral disc implant or spacer. The spacer is prepared or configured to retain an advantageous osteoinductive composition. In certain forms of the invention, a spacer is not utilized and the osteoinductive composition is injected, or otherwise disposed, into the intervertebral disc space, thus eliminating the open surgical procedures often necessary for spinal implant placement.

The present invention can combine minimally invasive surgery methods. The disc space may be prepared by minimally-invasive methods known to the skilled artisan, typically by making a small incision in the patient, such as no larger than about 30 mm, and inserting a cannula percutaneously into the patient through which the necessary tools can be delivered to, and manipulated at, the surgical site. The osteoinductive composition can be injected into the disc space.

Moreover, as desired or deemed medically prudent, instrumentation of the spine, including rods and plates, can advantageously be utilized in certain forms of the invention to maintain or restore desired disc space height and prevent disc space collapse after surgery during the fusion process.

The osteoinductive composition is combined with a pharmaceutically acceptable slow-release carrier. A preferred carrier is selected that allows a slow release of the osteoinductive factor. "Slow release" is defined herein to mean release of the osteoinductive factor at a rate that substantially reduces release of the osteoinductive factor from the carrier and thus substantially reduces migration, or diffusion, of the osteoinductive factor to tissue a distance from, typically adjacent to, the carrier or implant. The distant site can include scar tissue or other fibrous tissue, a hematoma, or other collection of blood cells or tissue, which can exhibit a propensity for bone tissue growth. Thus, "slow release" as defined herein also means release of the osteoinductive composition at a rate that substantially decreases bone tissue formation in undesired locations. Slow release also includes a rate of release wherein the half-life for release of the osteoinductive composition from the carrier is typically greater than about 2 days, preferably at least about 4 days, more preferably at least about 7 days and still more preferably at least about 14 days. With respect to the osteoinductive composition, the half-life refers to the amount of time it takes 50% of the mass of composition to be released from the carrier. In a one embodiment, the osteoinductive composition(s) are completed released from the carrier within about 8 to about 12 weeks.

In other forms, the carriers of the present invention are biodegradable and exhibit a half-life for maintaining their integrity. The carrier's half-life is the time period in which one half of the carrier's mass has been degraded or absorbed. In a one embodiment, the carrier's half-life is typically greater than about 2 days post implantation, preferably at least about 4 days, more preferably at least about 10 days and still more preferably at least about 14 days. Further, in other embodiments, the carrier is selected or formulated such that it is not completely degraded or its mass or volume approximates zero until at least about 8 weeks post implantation; more preferably the selected carrier is not completely degraded or its mass/volume reduced to zero before about 16 weeks post implantation.

The carrier can be selected and/or formulated to be flowable or injectable at a high temperature and which hardens at a lower temperature. The high temperature should not be at such a high level to cause tissue damage, and therefor, the high temperature is typically selected to be below about 60° C., more preferably below about 50° C., and still more preferably below about 45° C. The low temperature should be sufficiently high so the carrier maintains its selected conformation at body temperature and can take into account higher than normal body temperature levels caused by fever from infections or other physiological phenomenon. The low temperature level can be selected to be at least about 37° C. more preferably at least about 40° C.

In alternative embodiments, polymer based carriers are selected. The polymer based carriers are preferable a polymer matrix having pores such as can be found in sponge-like matrixes. The polymeric material can be a shape memory polymeric material as described in U.S. patent application Ser. Nos. 09/696,389, 09/696,146 or 09/696,715 all filed on Oct. 25, 2000. The polymeric material can be modified to slowly release an osteoinductive composition. For example, increasing the crosslinking between polymeric chains, combining the polymer with a collagen, gelatin or carboxymethylcellulose, or glycan, can serve to entrap an osteoinductive composition within the polymer matrix.

A wide variety of carriers may be used in the invention. Suitable carriers include polymers, such as, polylactic acid, polyglycolic acid, alternating copolymers of polylactic acid and polyglycolic acid, polyethylene glycol. These polymers may be formed into a matrix such as a sponge with voids for the infiltration with the osteoinductive material. Optionally, these polymers can be combined with one or more of carboxymethylcellulose hyaluronic acid, glycans such as glycosaminoglycans, gelatin, and/or collagen to effect suitable release profiles. The release rates from these polymers can be further influenced by chemical modification such as inducing and/or increasing polymer chain length and/or cross-linking, forming semi-interpenetrating polymer networks (SIPN) or interpenetrating polymer networks (IPN), star polymers polymer complexes and blends or polymer alloys and a combination thereof. Further, carboxymethylcellulose hyaluronic acid, glycans such as glycosaminoglycans, gelatin, and/or collagen can be modified to exhibit suitable release profiles by increasing the density of these compositions. Other carriers suitable for use with this invention include resorbable cements such as calcium phosphate, tricalcium phosphate and hydroxy apatite based cements. The resorbable cements may be substantially amorphous materials having the slow release properties described herein. In one form the carriers are formulated to have a higher affinity for selected osteoinductive compositions. These carriers can then be combined and/or compounded with the selected osteogenic compositions.

In one form, the carrier is provided as a calcium phosphate cement. Such calcium phosphate cements are preferably synthetic calcium phosphate materials that include a poorly or low crystalline calcium phosphate, such as a low or poorly crystalline apatite, including hydroxyapatite, available from Etex Corporation and as described, for example, in U.S. Pat. Nos. 5,783,217; 5,676,976; 5,683,461; and 5,650,176, and PCT International Publication Nos. WO 98/16268, WO 96/39202 and WO 98/16209, all to Lee et al. By use of the term "poorly or low crystalline" is meant to include a material that is amorphous, having little or no long range order and/or a material that is nanocrystalline, exhibiting crystalline domains on the order of nanometers or Angstroms. The calcium:phosphate ratio of the carrier is typically in the range of about 0.3 to about 0.7, more preferably about 0.4 to about 0.6.

In another form the carrier can be modified to exhibit a substantially closed porous structure. The osteoinductive material is preferable combined or blended with the carrier material or precursor prior to modification carrier into a substantially closed matrix. The osteoinductive material becomes trapped within the inner cells of the matrix. In use the carrier material slowly erodes, and as the carrier material erodes, the inner cells entraining the osteoinductive material are exposed. The exposed cells release the osteoinductive material contained therein. The biodegradation rate of the carrier can be varied as desired to vary the release rate of the osteoinductive material.

Utilizing the carrier described herein, bone formation is advantageously confined to the volume of the carrier. The bone that forms may thus be configured or otherwise shaped as the original shape of the carrier upon implantation. A carrier may confine or otherwise entrap the osteoinductive factor within the carrier so that the factor will be substantially released as the carrier is resorbed. Stated alternatively, the carrier will advantageously be substantially impermeable to efflux of the osteoinductive factor. It is further preferred that the carrier is selected so that substantially no osteoinductive factor migrates, or otherwise diffuses, into areas of unwanted bone formation as described above, or the amount of osteoinductive factor that may migrate into such areas will not be sufficient to substantially induce bone tissue generation.

A wide variety of osteoinductive factors may be used in the osteogenic composition, including bone morphogenetic proteins (BMPs), LIM mineralization proteins (LMPs), including LMP-1, growth differentiation factors (GDF), cartilage-derived morphogenic proteins (CDMP) and other growth factors such as epidermal growth factors, platelet-derived growth factors, insulin-like growth factors, fibroblast growth factors and transforming growth factors, including TGF-β and TGF-α, and combinations thereof A wide variety of bone morphogenetic proteins are contemplated, including bone morphogenetic proteins designated as BMP-2 through BMP-18, heterodimers thereof and combinations thereof. Proteins can be recombinant proteins, such as, recombinant human proteins. Suitable recombinant human bone morphogenetic proteins (rhBMPs) include rhBMP-2 and rhBMP-7.

BMPs are available from Genetics Institute, Inc., Cambridge, Mass. and may also be prepared by one skilled in the art as described in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al. All bone morphogenic proteins are contemplated whether obtained as above or isolated from bone. Methods for isolating bone morphogenetic protein from bone are described, for example, in U.S. Pat. No. 4,294,753 to Urist and Urist et al., 81 PNAS 371, 1984.

The osteoinductive composition may include the osteoinductive factors, or nucleotide sequences that encode the respective osteoinductive factors, so that the osteoinductive factor may be produced in vivo, in a pharmaceutically acceptable carrier. The nucleotide sequences can be operably linked to a promoter sequence and can be inserted in a vector, including a plasmid vector. A nucleic acid sequence can be "operably linked" to another nucleic acid sequence when it is placed in a specific functional relationship with the other nucleic acid sequence.

In other embodiments, cells may be transformed with nucleotide sequences encoding the osteoinductive factor and the osteoinductive composition will then include the transformed cells in a pharmaceutically acceptable carrier. In other forms, the osteoinductive composition includes a virus such as, for example, an adenovirus capable of eliciting intracellular production of a LIM mineralization protein.

When utilizing a resorbable cement carrier, a cell-sustaining component is further included in the carrier. The cell-sustaining component is one that provides nutrients to the cells so that they are able to produce the osteoinductive factor. The cell-sustaining component is also selected so that it does not substantially alter or otherwise modify the rate at which the carrier is resorbed or the rate at which the osteoinductive factor is released. Such cell-sustaining components include collagen, and various cell culture media utilized for ex vivo cell culture, including an infusible media such as normal saline supplemented with about 5% human serum albumen (HSA), Dulbecco's Modified Eagle's medium (DMEM), or RPMI 1640 supplemented with fetal bovine serum or serum-free medium formulations such as the X VIVO products, or the components include a combination thereof. In yet other forms of the invention, the nucleotide sequences may be combined directly with the carrier for delivery.

The amount of osteoinductive factor included in the carrier, and the amount applied to the treatment site, is typically an amount effective in forming new bone and eventual fusion of adjacent vertebrae. This amount will depend on a variety of factors including the nature of the osteoinductive factor, the osteoinductive potential of the factor, and the nature of the carrier, but will typically be about 0.5 mg BMP/ml carrier to about 4 mg BMP/ml carrier (corresponding to a weight ratio of BMP:dry carrier of about 1:2000 to about 1:250). The compositions may include about 1 mg BMP/ml carrier to about 3 mg BMP/ml carrier (corresponding to a weight ratio of BMP:dry carrier of about 1:1000 to about 1:333), but typically include at least about 2 mg BMP/ml carrier (corresponding to a weight ratio of BMP:dry carrier of at least about 1:500). The amount of the osteoinductive composition applied to the fusion site will also vary, but will typically be sufficient to deliver about 2 mg BMP to about 40 mg BMP, preferably about 4 mg BMP to about 20 mg BMP, and typically at least about 12 mg BMP.

Additionally, a wide variety of different implants or spacers can be used with the present invention. The implants or spacers may be configured to retain an osteoinductive composition as described herein. Implants may include chambers, channels, pores or other spaces in which the osteoinductive composition may be packed, placed or otherwise retained. The implants or spacers can be either resorbable/biodegradable or nonresorbable/biodegradable. Further the implants can bee intervertebral fusion devices, such as cages having a chamber therein, and optionally with end caps to further aid in retaining the osteoinductive composition. Examples of suitable implants may be found in U.S. Pat. Nos. 4,961,740; 5,015,247; 5,423,817, PCT Applications No. PCT/US01/08193 and PCT/US01/08073, and published PCT Application WO 99/29271.

Intervertebral fusion devices including the spinal implant and osteoinductive compositions described above are also provided which may advantageously be used to localize bone to desired areas as described herein during an intervertebral fusion procedure, especially a PLIF or a TLIF procedure.

In methods described herein utilizing a spinal implant, the osteoinductive composition is preferably disposed in, on or is otherwise associated with, the spinal implant described herein prior to inserting the implant in the intervertebral disc space. The ossteoinductive composition can be disposed in one or more chambers in an implant prior to inserting the implant into the intervertebral disc space. It is further realized that the osteoinductive composition may be retained or otherwise disposed on or in the implant while positioning the implant in the disc space or after it is so positioned. When disposing the composition on or in the implant after it is disposed in the disc space, it is preferred to utilize a carrier in a flowable form, which will preferably harden at about body temperature, although it is realized that the carrier may be in a wide variety of forms prior to disposing the carrier on or in the implant, including a flowable or non-flowable, hardenable or hardened form, as long as it will ultimately be in a hardened form or state in vivo at pharmacological temperature, pH, and in selected body fluids such as is found proximal to bone tissue and connective tissue.

Reference will now be made to specific examples illustrating the compositions, methods and devices described above. It is to be understood that the examples are provided to illustrate preferred embodiments and that no limitation to the scope of the invention is intended thereby.

EXAMPLE 1

Single-Level Posterolateral Fusion in Rhesus Monkeys

This example shows that posterolateral fusions performed in Rhesus monkeys with the bone substitute compositions described herein resulted in new bone formation that was confined to the volume occupied by the bone substitute compositions.

Animals and Experimental Design

Posterolateral transverse process fusions in 2 groups of 2 Rhesus monkeys were performed. One of the groups received rhBMP-2 in a carrier of standard α-bone substitute material (standard α-BSM®), a commercially available calcium phosphate cement purchased from Etex Corp., Cambridge, Mass. This standard material has a microporosity of 40%. The other group received rhBMP-2 in a carrier of modified α-BSM® (a bone substitute material from Etex with a porosity greater than 40%). In this second group, the left side of the spine was treated with the rhBMP-2 in a carrier of α-BSM® having 80% porosity (the porosity was increased by increasing the liquid content) and the right side of the spine was treated with α-BSM® having a porosity of about 80% from addition of collagen fibers to the standard α-BSM®. The extent of fusion was observed by Computer Tomography (CT) and X-ray analyses.

Preparation of BMP/Carrier

The rhBMP-2 was supplied in a buffer solution, pH 4.5 from Genetics Institute, Cambridge Mass. The rhBMP-2 solution was withdrawn from the provided vial with a needle and syringe and injected into a plastic mixing "bulb" containing the α-BSM® dry powder. The powder was then mixed by hand by kneading the plastic bulb for about 2-3 minutes until a mixture having a putty-like consistency is obtained. The tip of the bulb was cut off and the putty material applied, or otherwise administered, to the respective spinal posterolateral fusion site. The rhBMP-2 concentration was 2.1 mg BMP/ml of carrier. A composite comprising about 15 ng of BMP and about 7 ml of the putty-like material was used on each side of the spine.

Results

Figure 1:
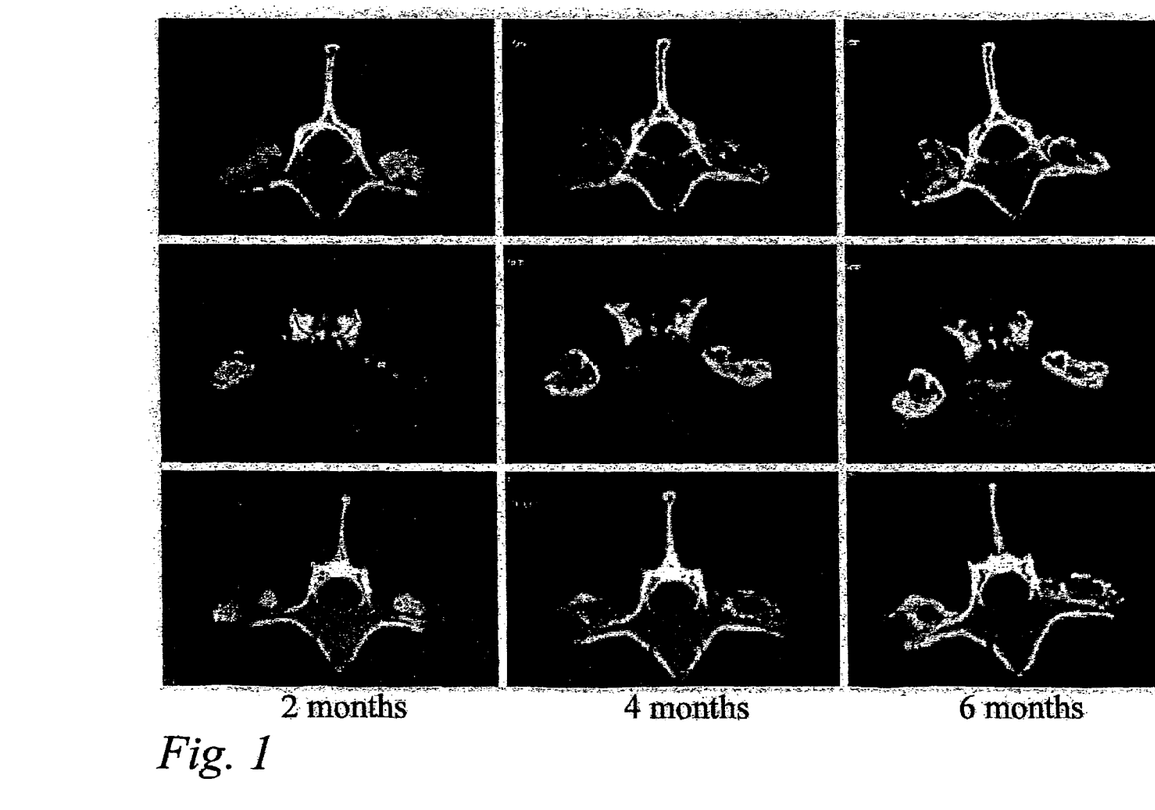
FIG. 1 is a series of scanned images of CT scans of three axial slices through a Rhesus monkeys' vertebra that were treated by posterolateral transverse process fusion using rhBMP-2 in a standard Etex calcium phosphate cement carrier. The CT scans were taken at 2, 4 and 6 months after implantation.
Figure 2:
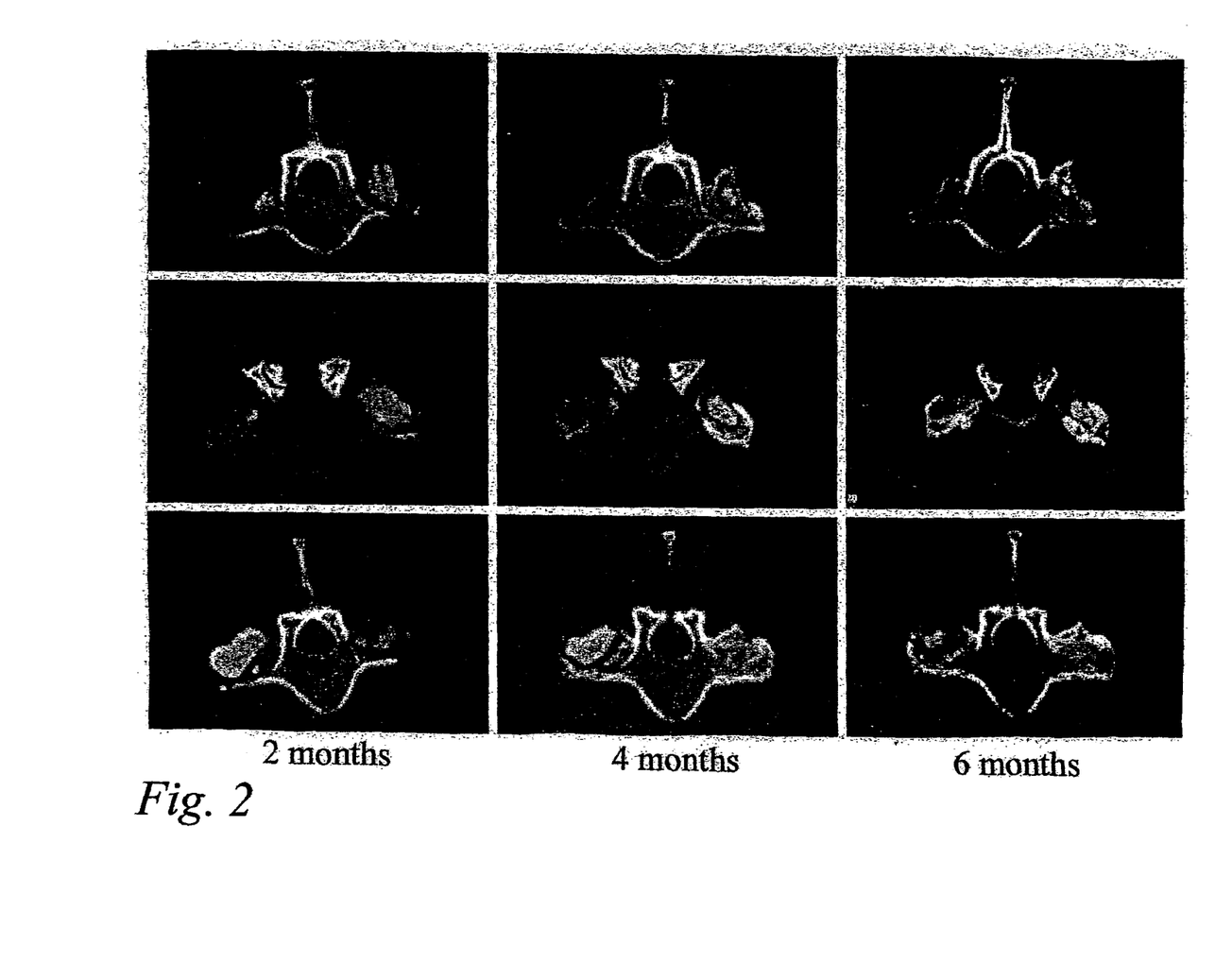
FIG. 2 is a series of scanned images of CT scans of the three axial slices through a Rhesus monkeys' vertebra that were treated by posterolateral transverse process fusion using rhBMP-2 in a modified Etex calcium phosphate cement carrier. The CT scans were taken at 2, 4 and 6 months after implantation.

It was found that fusion was achieved in all animals studied and that new bone formation was confined to the shape of the bone substitute material implanted across the transverse process. FIG. 1 is a series of scanned images of CT scans of taken at three different levels through the treated transverse process site at 2, 4 and 6 months post implantation for the first set of monkeys treated with rhBMP-2 in a standard Etex carrier. Similarly, FIG. 2 is a series of scanned images of CT scans of taken at three different levels through the treated transverse process site at 2, 4 and 6 months post implantation for the second set of monkeys treated with rhBMP-2 in a modified Etex carrier. It can be seen after analyzing FIGS. 1 and 2, that the shape and size of the fusion mass remains the same over time, indicating that the carrier retains the BMP within its matrix. As the carrier resorbs from the outside surface inward, it is replaced by new bone, thus resulting in precisely controlled bone formation.

Figure 3:
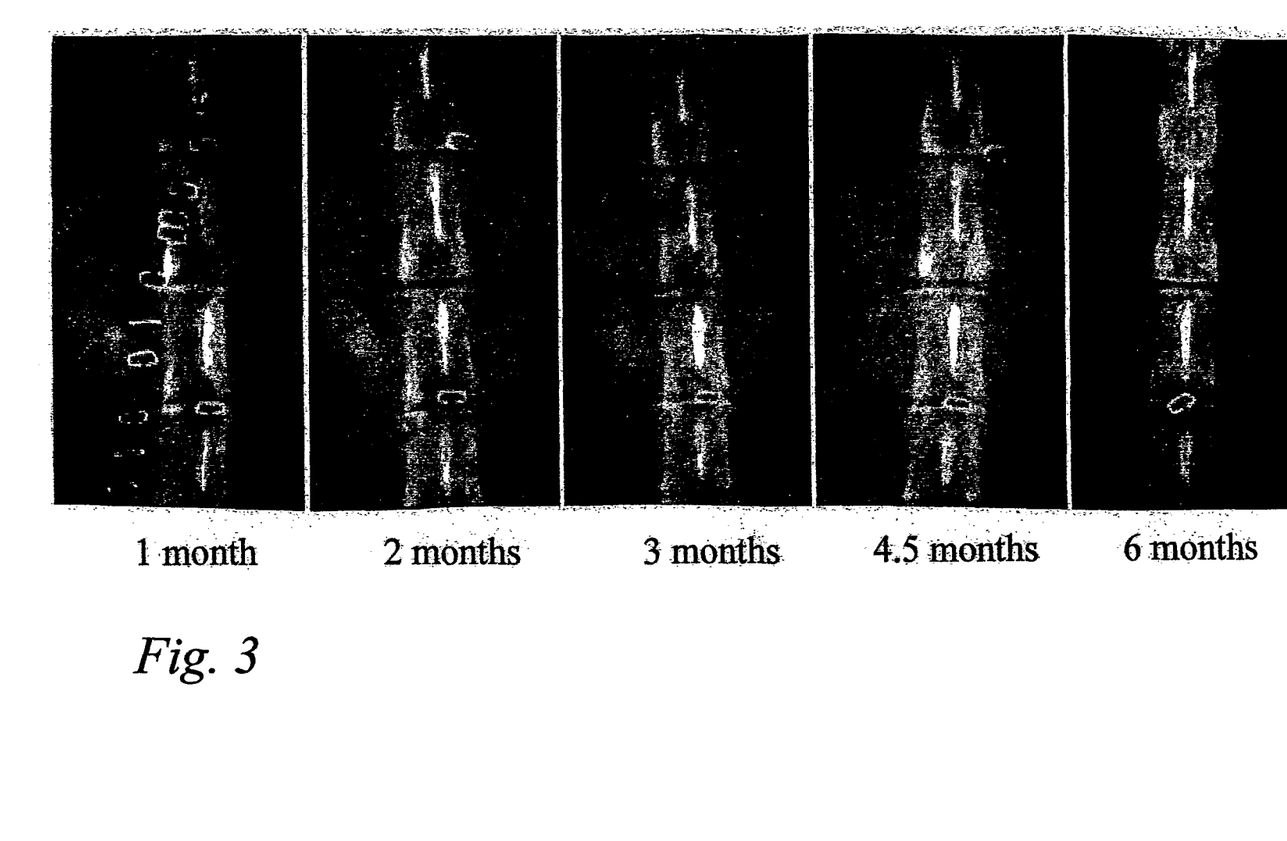
FIG. 3 is a series of scanned images of the whole spine X-ray of a monkey treated as in FIG. 1.
Figure 4:
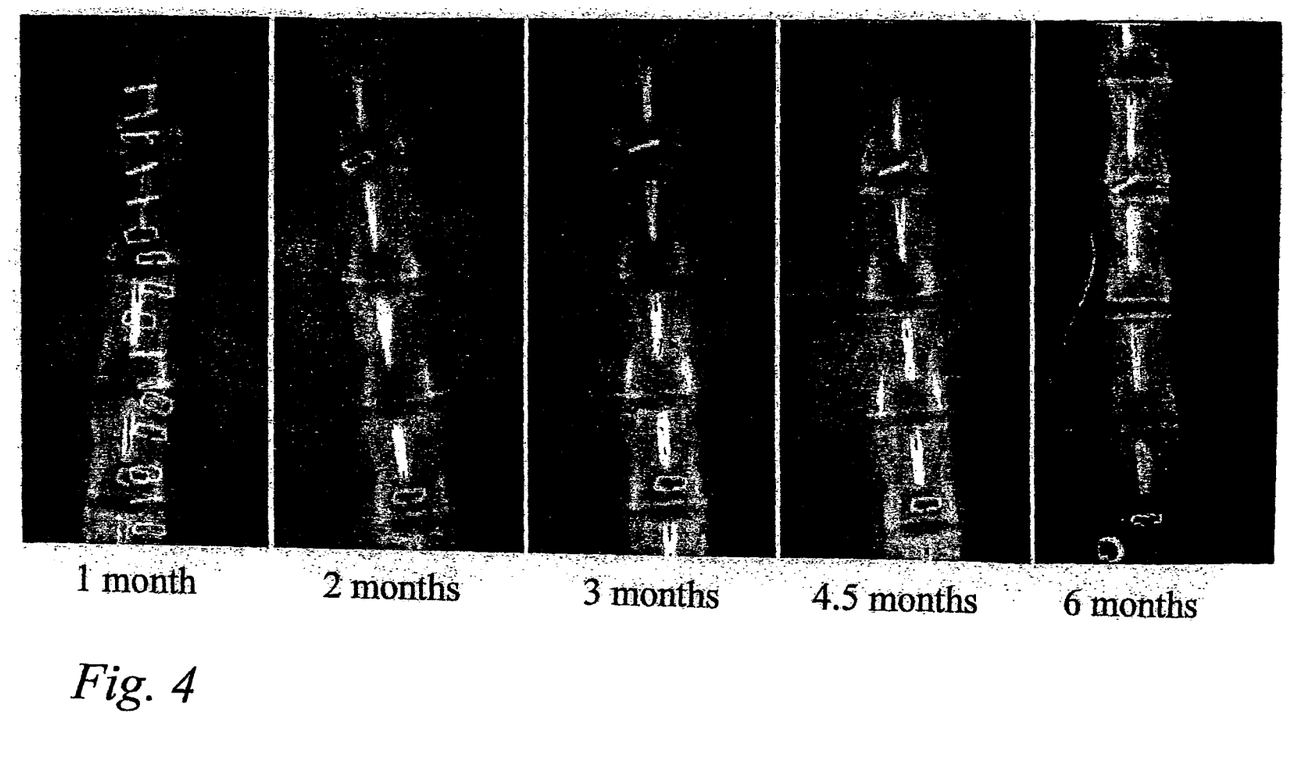
FIG. 4 is a series of scanned images of the whole spine X-ray of a monkey treated as in FIG. 2.

FIGS. 3 and 4 are scanned images of X-rays taken at 1, 2, 4.5 and 6 months post implantation of the spinal column of the monkeys corresponding to the CT scans in FIGS. 1 and 2, respectively. As seen in FIGS. 3 and 4, the α-BSM® resorbs over time and is replaced by new bone across the transverse process.

EXAMPLE 2

Pharmacokinetic Study of the Release of rhBMP-2 from α-BSM and ACS

The release kinetics for rHBMP-2 from α-BSM and ACS evaluated in a rabbit ulna osteotomy. A 125I-rhBMP-2/α-BSM or 125IrhBMP-2/ACS product was surgically implanted in a rabbit ulna osteotomy. Assessment of the radioactivity at the implant site were made as soon as possible following surgery. Additionally assessments were made periodically thereafter including at 1, 2, 3, 4, 7, 14 and 21 days after surgery.

The rhBMP-2 was radiolabeled with $^{125}$I using the iodogen technique. The following a typical procedure. An 80 μg/mL solution of iodogen reagent (Pierce, Rockford, Ill.) was prepared in chloroform. An aliquot of this solution (50 μL) was placed into a micro-eppendorf tube and evaporated to dryness under a gentle stream of nitrogen. To this tube was added 30 μg of rhBMP-2, sufficient MFR 00842 buffer to bring the volume up to 50 μL, and 1-2 mCi of carrier-free $^{125}$I (Dupont NEN Research Product, Boston Mass.). This solution was incubated at room temperature for 30 minutes with gentile agitation. Following incubation, the solution was added to a NAP-5 column (Sephadex G-25, Pharmacia, Uppsala, Sweden), that had been preequilibrated with 1 column volume of MFR 00842 buffer. The column contains about 100 μL of MFR 00842 when the reaction mixture was added. The iodinated protein was eluted from the column with MFR 00842 buffer and 500 μL fractions were collected. Total $^{125}$I content in each fraction was determined by adding 5 μL of each fraction to a polystyrene tube containing 295 μL of bovine serum albumin (BSA, 10 mg/mL) and 200 μL phosphate-buffered saline (PBS). Each tube was counted in a gamma counter for total activity. Trichoroacetic acid (TCA)-precipitable radioactivity was determined as follows: 500 μL of 20% TCA was added to each tube and centrifuged at approximately 700×g for 10 minutes. Five hundred μL of the supernatant was counted, and soluble radioactivity was determined by the equation:

$$([2\times\text{supernatant CPM}]+\text{total CPM})\times 100$$

Fractions that were less than 5% soluble were pooled and stored at 4° C. Each iodination yields 30 μg of rhBMP-2 in 400 μL of buffer with a CPM (counts per minute) of approximately $3.3\times10^9$.

The α-BSM test implant was prepared as described above in Example 1. The α-BSM clinical formulation exhibited an L:S ratio of 0.85; the wet formulation had an L:S ratio of 1.0.

The ACS an absorbable collagen source (Helistat® available from Integra Life Sciences Holdings Corp. of Plainsboro, N.J.), was prepared by pipetting a sample of the $^{125}$I-rhBMP-2 in a buffer (OR 00926) onto the collagen source pieces. The test implants were allowed to set for about 5 minutes and implanted in the subject rabbit as soon as possible after this time.

Assessment of the radioactivity of the site was made using gamma scintigraphy (Siemans Orbitor Gamma Camera). In order to quantify the gamma camera images, a phantom must be developed. The phantom was designed based on the attenuation of the activity seen from implantation of a vial containing a known quantity of $^{125}$I labeled rhBMP-2 at the implantation site in a rabbit cadaver. The phantom was assessed at each time point to account for decay of the $^{125}$I over time. Following surgical closure (5 to 10 minutes after implantation), a time zero (T0) assessment of the radioactivity at the site was made. Thereafter, animals were anesthetized, if necessary, and assessments were made.

Figure 5:
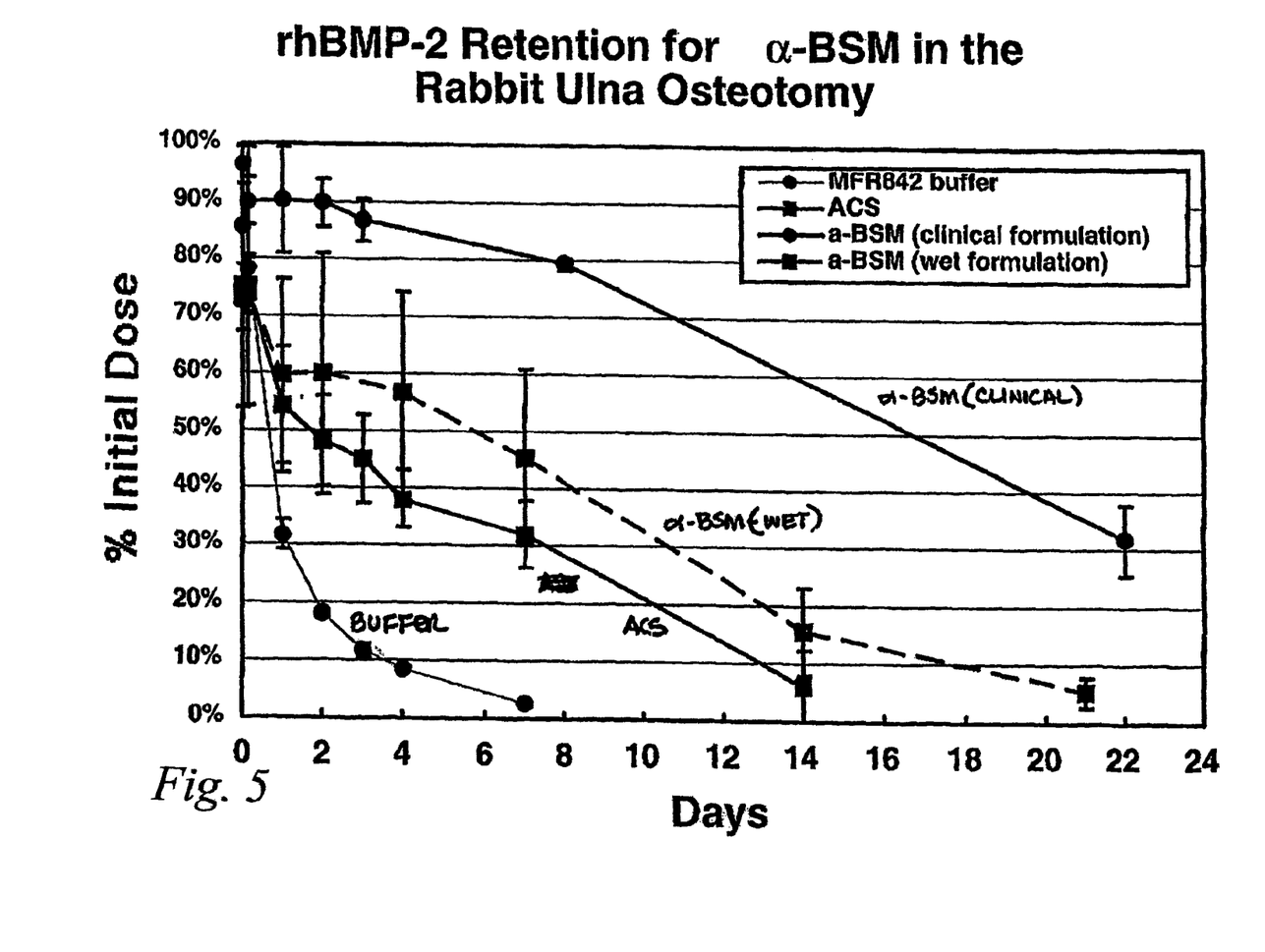
FIG. 5 is a graph illustrating rhBMP-2 release kinetics from Etex cement.

FIG. 5 is a graph illustrating the retention of rhBMP-2 in α-BSM prepared as and measured as described above. It can be seen from the graphs that the osteogenic composition is released from the BSM carrier at a much slower rate than from the ACS collagen sponge carrier.

Figure 6:
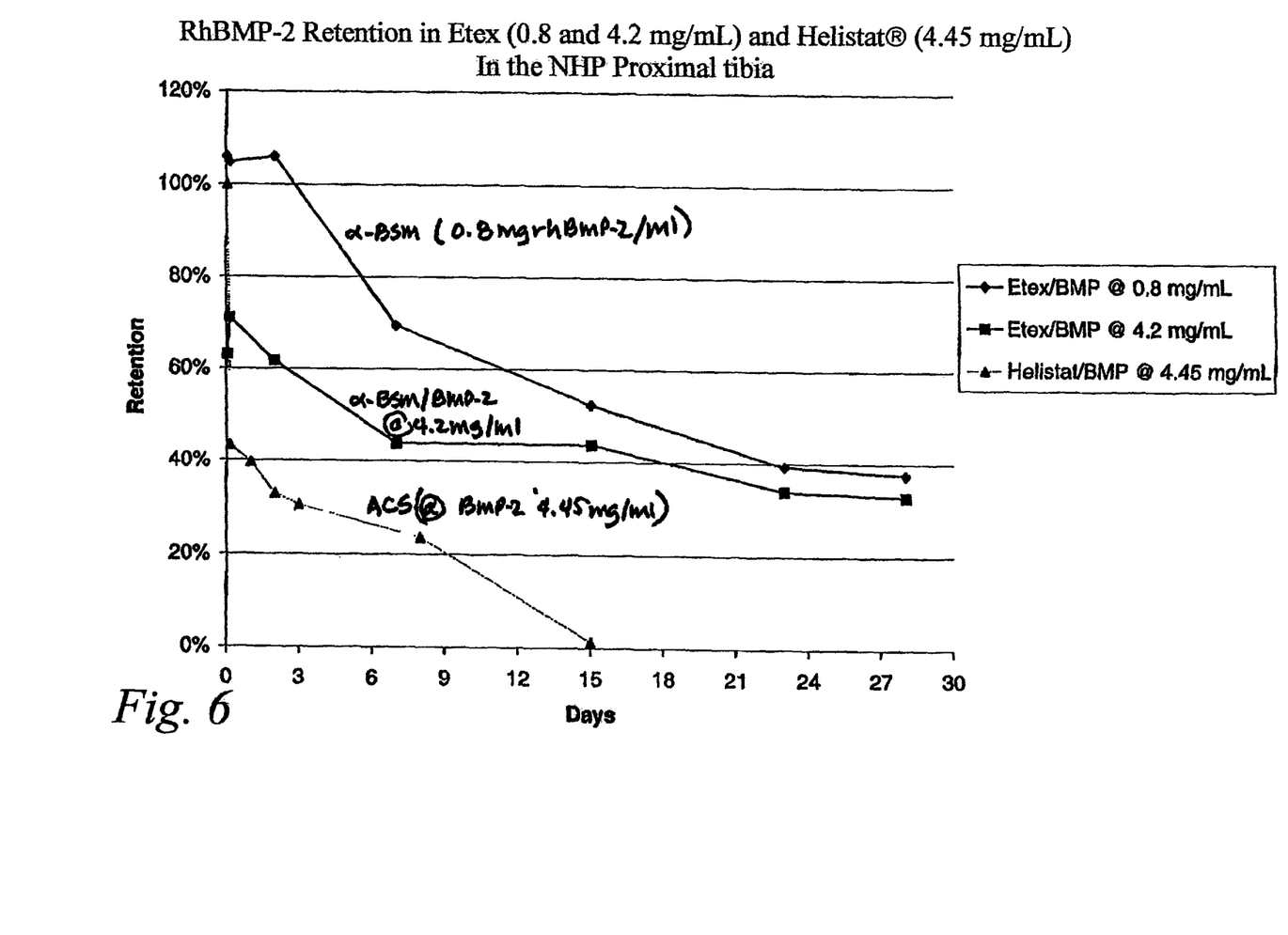
FIG. 6 is a graph illustrating the retention profile of rhBMP-2 in Etex cement.

FIG. 6 is a graph illustrating the release rate kinetics of rhBMP-2 from α-BSM prepared as described above. These results indicate that the retention rate of rhBMP-2 in the α-BSM was much greater than the retention of the same rhBMP-2 in an absorbable collagen source, Helistat®.

While the embodiments of invention have been illustrated and described in detail in the drawings and foregoing description, the same is to be considered as illustrative and not restrictive in character, it being understood that all changes and modifications that come within the spirit of the invention are desired to be protected. In addition, all references cited herein are hereby incorporated by reference in their entirety.

What is claimed is:

1. An intervertebral fusion device comprising an osteoinductive composition for treating bone defects, the osteoinductive composition present in an amount effective to induce bone growth to form a bone mass in a location for fusing adjacent vertebrae, said composition comprising:
   a biodegradable collagen carrier comprising a polymer matrix and pores forming a sponge matrix,
   bone morphogenetic protein 2 (BMP-2) entrained within the carrier, and
   LIM mineralization protein-1 (LMP-1) entrained within the carrier;
   wherein the bone morphogenetic protein 2 is present in an amount of 0.5 mg/ml to 4 mg/ml of the biodegradable collagen carrier,
   wherein the carrier further comprises calcium phosphate and has a calcium to phosphate (Ca/P) ratio of about 0.4 to about 0.6, and the carrier has a porosity of greater than 40%,
   wherein the osteoinductive composition is sufficient to deliver 2 mg of bone morphogenetic protein 2 to 40 mg of bone morphogenetic protein 2, and
   wherein the carrier is configured to be substantially impermeable to efflux of the entrained osteoinductive composition in vivo sufficiently that the formed bone mass is confined to the volume of the carrier when implanted, and wherein the carrier gradually exposes the entrained osteoinductive composition at said location as it degrades.

2. An intervertebral fusion device of claim 1, wherein said calcium phosphate comprises tricalcium phosphate.

3. An intervertebral fusion device of claim 2, wherein said composition further comprises hydroxyapatite.

4. An intervertebral fusion device of claim 1, wherein said bone morphogenetic protein 2 is a recombinant human bone morphogenetic protein.

5. An intervertebral fusion device of claim 1, wherein said composition further comprises transforming growth factors, insulin-like growth factors, epidermal growth factors, platelet-derived growth factors and fibroblast growth factors.

6. An intervertebral fusion device of claim 1, wherein less than about 50% by weight of the osteoinductive composition is released from the carrier after about 2, 4, 7, 10 or about 14 days post implantation.

* * * * *